United States Patent
Shimizu

(10) Patent No.: US 10,022,494 B2
(45) Date of Patent: Jul. 17, 2018

(54) INFUSION PUMP

(71) Applicant: TERUMO KABUSHIKI KAISHA, Tokyo (JP)

(72) Inventor: Nobutaka Shimizu, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 565 days.

(21) Appl. No.: 14/664,396

(22) Filed: Mar. 20, 2015

(65) Prior Publication Data

US 2015/0314066 A1  Nov. 5, 2015

Related U.S. Application Data

(63) Continuation of application No. PCT/JP2012/006216, filed on Sep. 27, 2012.

(51) Int. Cl.
*A61M 5/168* (2006.01)
*A61M 5/158* (2006.01)
(Continued)

(52) U.S. Cl.
CPC .... *A61M 5/16831* (2013.01); *A61M 5/14228* (2013.01); *A61M 5/158* (2013.01);
(Continued)

(58) Field of Classification Search
CPC .............. A61M 5/142; A61M 5/14228; A61M 5/16831; A61M 2005/16863;
(Continued)

(56) References Cited

U.S. PATENT DOCUMENTS 4,369,780 A * 1/1983 Sakai ................ A61M 5/16854
128/DIG. 12
4,936,760 A * 6/1990 Williams .............. A61M 5/142
417/478

(Continued)

FOREIGN PATENT DOCUMENTS

JP  H01-249064  10/1989
JP  H06-30993    2/1994

(Continued)

OTHER PUBLICATIONS

International Search Report for International Patent Application No. PCT/JP2012/006216, dated Jan. 8, 2013, 4 pages.
Extended European Search Report for European Patent Application No. 12885703.4, dated Apr. 14, 2015, 7 pages.

*Primary Examiner* — Kami A Bosworth
(74) *Attorney, Agent, or Firm* — Sheridan Ross P.C.

(57) ABSTRACT

Provided is an infusion pump in which one or more occlusion sensors includes a Hall element detecting a variation in magnetic flux, of one or more magnets, generated with movement of a plunger caused by a variation of an infusion tube in a radial direction that results from an occlusion of the infusion tube, and changing the variation of an infusion tube in the radial direction into an output voltage. When increasing a movement distance of the plunger to a plurality of predetermined positions D1 to D4, a control unit obtains linearity of output voltages PV1 to PV4 of the Hall element with respect to movement distances to a plurality of positions D1 to D4 by applying a plurality of predetermined impression voltages BE1 to BE16 to the Hall element to select from the plurality of impression voltages applied for each of the movement distances to the plurality of positions.

8 Claims, 9 Drawing Sheets

(51) Int. Cl.
*A61M 5/50* (2006.01)
*A61M 5/142* (2006.01)

(52) U.S. Cl.
CPC ... *A61M 5/5086* (2013.01); *A61M 2005/1585* (2013.01); *A61M 2005/1588* (2013.01); *A61M 2005/16863* (2013.01); *A61M 2005/16868* (2013.01); *A61M 2005/16872* (2013.01); *A61M 2205/3317* (2013.01)

(58) Field of Classification Search
CPC ......... A61M 2005/16868; A61M 2005/16872; A61M 2205/3317; F04B 43/08; F04B 43/084; F04B 49/00; F04B 49/08; F04B 2205/05; F04B 2207/04; F04B 2207/041; F04B 2207/0411
See application file for complete search history.

(56) References Cited

U.S. PATENT DOCUMENTS

| | | |
|---|---|---|
| 5,098,380 A | 3/1992 | Aizawa et al. |
| 6,213,723 B1 | 4/2001 | Danby et al. |
| 9,005,159 B2 * | 4/2015 | Lee .................. A61M 5/14228 604/67 |

FOREIGN PATENT DOCUMENTS

| | | |
|---|---|---|
| JP | H06-254159 | 9/1994 |
| JP | H11-508017 | 7/1999 |
| JP | 2010-200775 | 9/2010 |
| WO | WO 1977/037703 | 10/1997 |
| WO | WO 2007/079016 | 7/2007 |

\* cited by examiner

INFUSION PUMP

CROSS REFERENCE TO RELATED APPLICATIONS

This Application is a continuation of and claim priority to PCT/JP2012/006216, filed Sep. 27, 2012, entitled "INFUSION PUMP," which is incorporated herein by reference in its entirety for all that it teaches and for all purposes.

TECHNICAL FIELD

The embodiments herein relate generally to an infusion pump for delivering drug and the like by causing a distal opening portion of an endovascular indwelling catheter or an indwelling needle which communicates with an infusion tube to indwell inside a vein or an intestinal tract of a patient.

BACKGROUND

An infusion pump is used in an intensive care unit (ICU) or the like and is adopted to deliver treatment of drug for a patient at relatively high accuracy for a relatively long period of time. A predetermined drug bag (an infusion bag) is arranged on the top of the infusion pump and an infusion tube suspended from the drug bag is interposed between a main body and an opening/closing door. The infusion tube is accommodated in the main body and is held therein by closing the opening/closing door. In the main body of the infusion pump, an outer circumferential surface of the infusion tube set in a home position is interposed between a plurality of fingers inside the main body and an inner surface of the opening/closing door. The infusion pump is a peristaltic infusion pump which delivers drug to a patient through an endovascular indwelling catheter or an indwelling needle by causing the plurality of fingers to sequentially press the outer circumferential surface of the infusion tube along a longitudinal direction (See JP2010-200775A).

In the infusion pump disclosed in JP 2010-20075A, the infusion tube is held in the main body of the infusion pump and passes therethrough vertically downward from the top. In contrast, there is a proposed infusion pump in which the infusion tube passes through the main body of the infusion pump in a horizontal direction to be held therein. Such a structure of the infusion tube passing through the main body of the infusion pump in the horizontal direction to be held therein is employed because of an advantage in which the infusion tube is not a hindrance even though a plurality of the infusion pumps are vertically positioned in a stacked state and the infusion tubes are held in a bunch, being different from the infusion tube which is held in the main body of the infusion pump passing therethrough vertically downward from the top. For example, it is decided previously so as to arrange an upstream side of the infusion tube at a portion on the right to the main body of the infusion pump and to arrange a downstream side of the infusion tube at a portion on the left to the main body of the infusion pump. In this case, if the upstream side of the infusion tube is arranged at the right side portion of the main body of the infusion pump, and the downstream side of the infusion tube is arranged at the left side portion of the main body of the infusion pump, a drug can be delivered along a preset delivering direction from the upstream side to the downstream side, thereby being properly delivered to a patient.

SUMMARY

In such an infusion pump as described above, an occlusion sensor, which detects an occlusion of an infusion tube, is arranged. The occlusion sensor has one Hall element which is arranged on a main body side of the infusion pump and two magnets which are arranged in a plunger. If the infusion tube is occluded, there is an occurrence of a variation of the infusion tube in diametral dimensions. As the plunger having the two magnets moves in accordance with the variation of the infusion tube in the diametral dimensions, the two magnets move so as to vary a relative distance with respect to a Hall element. A control unit detects an occlusion state of the infusion tube from a variation of an output of the Hall element generated in response to an occlusion of the infusion tube.

Incidentally, when setting the occlusion sensor in the main body of the infusion pump, an output voltage of the Hall element is obtained at two positions of the plunger which is previously set by an assembler for convenience, thereby obtaining linearity of the output voltage of the Hall element with respect to a movement distance of the plunger. Therefore, linearity of the output voltage of the Hall element is likely to be inaccurate, and the occlusion state of the infusion tube cannot be accurately detected.

Thus, the present invention aims to provide an infusion pump in which linearity of the output voltage of the Hall element in the occlusion sensor with respect to a variation of the infusion tube in diametral dimensions can be accurately obtained and an occlusion state of the infusion tube can be accurately detected.

In addition, the embodiments herein aim to provide an infusion pump in which it can be also determine whether the infusion tube is reliably set to a predetermined position in the infusion pump.

Solution to Problem

According to the embodiments, there is provided an infusion pump for delivering any one of a drug, blood, and a nutrient by causing a distal opening portion of an endovascular indwelling catheter or an indwelling needle, which communicates with an infusion tube, to indwell inside a vein or an intestinal tract of a patient. The infusion pump is characterized by including an occlusion sensor that detects an occlusion of the infusion tube when delivering the drug, and a control unit that is supplied with an output voltage of the occlusion sensor. The occlusion sensor includes a movement member which has a plurality of magnets and is arranged in a linearly movable manner. The occlusion sensor includes a Hall element which is fixed to the infusion pump on a main body side, detects a variation in magnetic fluxes of the plurality of magnets generated in accordance with a linear movement of the movement member following after a variation of the infusion tube in a radial direction that results from the occlusion of the infusion tube, and changes the variation of the infusion tube in the radial direction into the output voltage. When increasing a movement distance of the movement member to a plurality of predetermined positions, the control unit is configured to obtain linearity of the output voltage of the Hall element with respect to the movement distances to the plurality of positions by applying a plurality of predetermined impression voltages to the Hall element for each of the movement distances to the plurality of positions so as to select from the plurality of impression voltages applied for each of the movement distances to the plurality of positions.

According to the configuration described above, when increasing the movement distance of the movement member to the plurality of predetermined positions, the control unit may be configured to obtain linearity of the output voltage of the Hall element with respect to the movement distances to the plurality of positions by applying the plurality of predetermined impression voltages to the Hall element for each of the movement distances to the plurality of positions so as to select from the plurality of impression voltages applied for each of the movement distances to the plurality of positions. Accordingly, linearity of the output voltage of the Hall element in the occlusion sensor with respect to a variation of the movement distance of the movement member, that is, a variation of the infusion tube in diametral dimensions can be accurately obtained and an occlusion state of the infusion tube can be accurately detected.

The movement distance corresponding to the output voltage having linearity is 2 to 3 times a swelling rate of the infusion tube.

According to the configuration described above, it is possible not only to increase a margin with respect to a threshold value in detection of occlusion and to achieve appropriate sensitivity so as to allow detection of occlusion to be accurate but also to provide a plurality of the threshold values in detection of occlusion as necessary.

It is determined that the infusion tube deviates from a tube setting portion if the output voltage is not in a region of linearity.

The control unit can have an impression voltage table storing the plurality of impression voltages which are respectively predetermined for each of the movement distances to the plurality of positions.

According to the configuration described above, with reference to the impression voltage table, the control unit can apply the plurality of predetermined impression voltages to the Hall element for each of the movement distances to the plurality of positions. Thus, linearity of the output voltage of the Hall element in the occlusion sensor with respect to the variation of the infusion tube in diametral dimensions can be simply obtained.

The infusion pump can further include warning means that issues a warning in response to a command of the control unit if the occlusion sensor detects an occlusion of the infusion tube.

According to the configuration described above, a health care worker can be notified of the occlusion state of the infusion tube through a warning. Thus, a delivering operation can be immediately stopped in case of an occlusion.

The infusion pump can further include a temperature sensor that detects an environmental temperature of the infusion tube. The control unit changes a threshold value of the movement distance of the movement member in response to a signal from the temperature sensor in accordance with a value of the environmental temperature.

According to the configuration described above, an occlusion of the infusion tube can be detected in accordance with a swelling state of the infusion tube in the radial direction depending on the environmental temperature.

A display unit displaying information and an operation panel portion having an operation button can be arranged in an upper portion of a main body of the infusion pump, and the infusion tube for delivering the drug is arranged in a region of a lower portion of the main body of the infusion pump.

According to the configuration described above, a health care worker can perform delivering of a drug by using the infusion pump while confirming the information on the display unit in the upper portion of the main body. Then, the health care worker can operate the operation button of the operation panel portion while confirming the information on the display unit in the upper portion of the main body.

Advantageous Effects the Embodiments

According to the embodiments, it is possible to provide an infusion pump in which linearity of an output voltage of a Hall element in an occlusion sensor with respect to a variation of an infusion tube in diametral dimensions can be accurately obtained and an occlusion state of the infusion tube can be accurately detected.

DETAILED DESCRIPTION

Hereinafter, embodiments will be described in detail with reference to the drawings.

Since the below-described embodiments is an example, the embodiment is applied with various types of limitations which are optional. However, the scope of the embodiment is not limited to the aspects thereof unless there is disclosure particularly limiting the embodiments in the following description.

Figure 1:
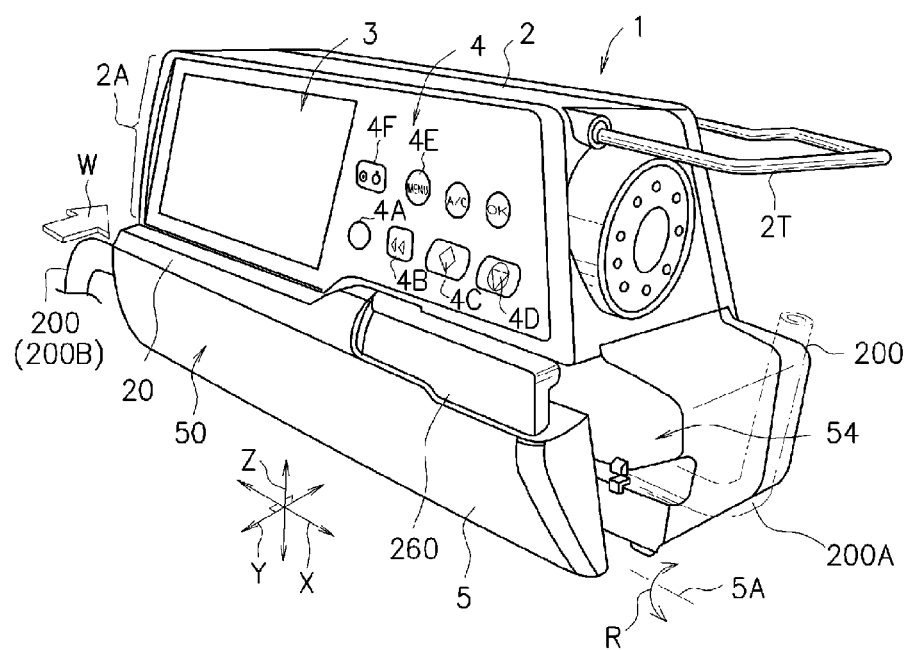
FIG. 1 is a perspective view illustrating an embodiment of an infusion pump.
Figure 2:
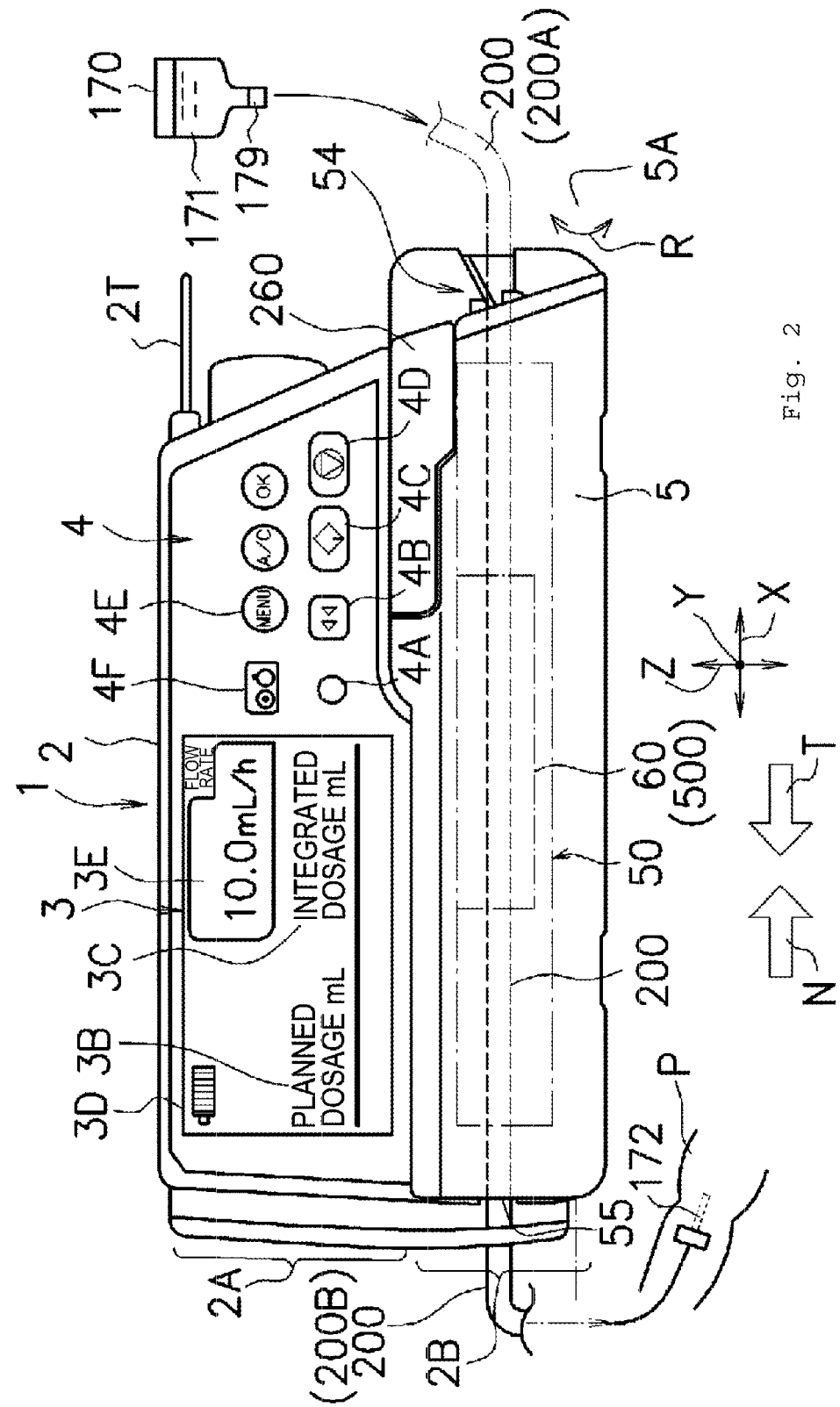
FIG. 2 is a diagram of the infusion pump illustrated in FIG. 1 when seen in a W-direction.

FIG. 1 is a perspective view illustrating an embodiment of an infusion pump. FIG. 2 is a diagram of the infusion pump illustrated in FIG. 1 when seen in a W-direction.

An infusion pump 1 illustrated in FIGS. 1 and 2 is a continuous infusion pump which is used for a patient, for example, in infusion treatment of a drug (also referred to as a drug solution) such as an anticancer drug, an anesthetic, a chemotherapeutic and the like, infusion treatment of a nutrient, a blood transfusion and the like, for example, in intensive care units (ICU, CCU, NICU) or the like at relatively high accuracy for a relatively long period of time.

The infusion pump 1, for example, is used to select a drug to be used from a drug library and to deliver the selected drug. The drug library is drug information of a dosage setting group of a drug including the previously registered drug names in a drug library database (DB). A health care worker can select the drug and can set the drug without performing complicated dosage setting every time by adopting the drug library.

As illustrated in FIG. 2, the infusion pump 1 can accurately deliver liquid to the inside of a blood vessel of a patient P from a drug bag 170 filled with the drug 171 through a Klemme 179, an infusion tube 200, and an indwelling needle 172. Drug is also referred to as an infusion solution. An infusion tube is also referred to as an infusion line.

The infusion pump 1 has a main body cover 2 and a handle 2T. The handle 2T can be stretched in an N-direction and can be accommodated in a T-direction. The main body cover 2 is also referred to as a main body and is integrally molded with a molding resin material which is chemically resistant. The main body cover 2 has a drip-proof treated structure which can prevent the inside of the infusion pump 1 from being penetrated by the drug even if the drug or the like is splashed over the main body cover. The main body cover 2 has such a drip-proof treated structure because there may be a case where the drug 171 in the drug bag 170 arranged in an upper portion is spilt, or an antiseptic solution or the like used in the vicinity thereof is splashed and adheres thereto.

Firstly, components arranged in the main body cover 2 of the infusion pump 1 will be described.

As illustrated in FIGS. 1 and 2, a display unit 3 and an operation panel portion 4 are arranged in an upper portion 2A of the main body cover 2. The display unit 3 is an image display apparatus, and a color liquid crystal display apparatus is used, for example. The display unit 3 can display information not only by notation in English but also by notation in multiple foreign languages as necessary. The display unit 3 is arranged at an upper left position in the upper portion 2A of the main body cover 2, that is, on an upper side of an opening/closing cover 5. The upper portion 2A of the main body cover 2 is the upper half portion of the main body cover 2. The lower portion 2B of the main body cover 2 is the lower half portion of the main body cover 2.

In the upper portion 2A of the main body cover 2 of the infusion pump 1, the display unit 3 for displaying information and the operation panel portion 4 including a plurality of operation buttons are arranged. The lower portion 2B of the main body cover 2 of the infusion pump 1 is a region in which the infusion tube 200, that is, a delivery member for delivering the drug is arranged. Accordingly, a health care worker can perform delivering of the drug by using the infusion pump 1 while confirming information on the display unit 3 in the upper portion 2A of the main body cover 2. Then, the health care worker can operate the operation buttons of the operation panel portion 4 while confirming the information on the display unit 3 in the upper portion 2A of the main body cover 2. Therefore, the infusion pump 1 has favorable operability.

In FIG. 2, as an example, the display unit 3 displays a display section 3B for a planned dosage (mL) of drug, a display section 3C for an integrated dosage (mL) of drug, a display section 3D for a charge history, a display section 3E for a flow rate (mL/h), and the like. However, in the display unit 3, illustrated in FIG. 1, the aforementioned display contents are omitted in order to simplify the drawing. The display unit 3 can additionally display a warning message. For example, by lighting a backlight of a light emitting diode (LED), the display unit 3 can change the display from "a yellow display screen" to "a white display screen" which is a warning screen issued to a health care worker.

The operation panel portion 4 is arranged on the right side of the display unit 3 in the upper portion 2A of the main body cover 2. As the operation buttons in the illustrated example, a lamp 4A (formed with an LED, blinking or being lit in green during a normal operation, and blinking or being lit in red during an abnormal operation) which functions as an operational indicator, a fast-delivering switch button 4B, a start switch button 4C, a stop switch button 4D, a menu selection button 4E, a power switch 4F, and the like are arranged in the operation panel portion 4, for example.

As illustrated in FIG. 1, the opening/closing cover 5 as a lid member is provided in the lower portion 2B of the main body cover 2 so as to be able to be in open and closed states in an R-direction having a rotary shaft 5A as the center. The opening/closing cover 5 is a plate-like lid member formed to be elongated along an X-direction. A tube setting portion 50 and a liquid delivering drive unit 60 are arranged inside the opening/closing cover 5. The infusion tube 200 made of a flexible thermoplastic resin such as soft vinyl chloride and the like, for example, is set to the tube setting portion 50. As the opening/closing cover 5 is in the closed state, the infusion tube 200 can be horizontally set in the tube setting portion 50 along the X-direction (the T-direction).

The X-direction, a Y-direction, and a Z-direction in FIGS. 1 and 2 are orthogonal to each other. The Z-direction is a vertical direction. The X-direction is a transverse direction of the infusion pump 1 parallel to the T-direction which is a delivering direction. The Y-direction is a front-rear direction of the infusion pump 1.

Figure 3:
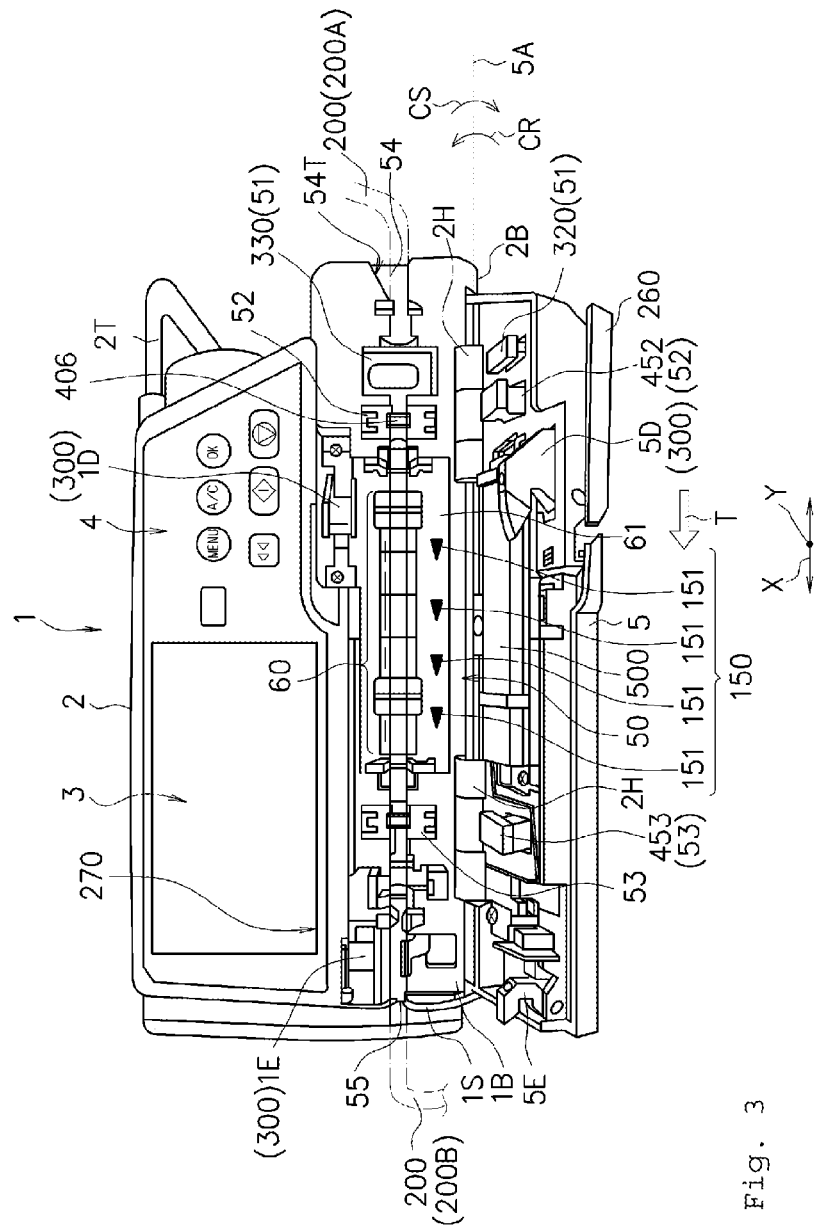
FIG. 3 is a perspective view illustrating an opening/closing cover of the infusion pump in an open state.

FIG. 3 is a perspective view illustrating the tube setting portion 50 for setting the infusion tube 200 by causing the opening/closing cover 5 of the infusion pump 1 illustrated in FIGS. 1 and 2 to be in an open state.

As illustrated in FIG. 3, the tube setting portion 50 and the liquid delivering drive unit 60 are provided on a main body lower portion 1B side of the infusion pump 1. The tube setting portion 50 and the liquid delivering drive unit 60 are provided along the X-direction at a lower portion of the display unit 3 and the operation panel portion 4. As illustrated in FIG. 2, the tube setting portion 50 can be covered with the opening/closing cover 5 by closing the opening/closing cover 5 in a CR-direction having the rotary shaft 5A as the center.

A health care worker can set the infusion tube 200 in the tube setting portion 50 and close the opening/closing cover 5 while confirming the information on the display unit 3 in the upper portion 2A of the main body cover 2. Then, the health care worker can operate the operation buttons of the operation panel portion 4 while confirming the information on the display unit 3 in the upper portion 2A of the main body cover 2. Accordingly, in medical sites, operability of the infusion pump 1 can be improved.

As illustrated in FIG. 3, the tube setting portion 50 includes an air bubble sensor 51, an upstream occlusion sensor 52, a downstream occlusion sensor 53, a tube clamp portion 270, a first infusion tube guide portion 54 at a position on the right side, and a second infusion tube guide portion 55 at a position on the left side.

As illustrated in FIG. 3, in the vicinity of the tube setting portion 50, there is provided an infusion tube setting direction display portion 150 for clearly displaying the T-direction as the proper delivering direction when setting the infusion tube 200. For example, the infusion tube setting direction display portion 150 is configured to include a plurality of arrows 151. For example, the infusion tube setting direction display portion 150 may be directly printed on the lower portion of the tube setting portion 50 or may be printed on a sticker-like member so as to be pasted on the lower portion of the tube setting portion 50. The infusion tube setting direction display portion 150 is arranged in order to clarify the delivering direction (the T-direction) as the proper direction for the drug 171 which is delivered through the infusion tube 200 set inside the opening/closing cover 5.

Accordingly, it is possible to clarify the T-direction as the delivering direction of drug delivered through the infusion tube 200 when a health care worker undoes the opening/closing cover 5 of FIG. 3 in a CS-direction, opens the tube setting portion 50, and causes the infusion tube 200 to be set in the tube setting portion 50. Therefore, it is possible for a health care worker to be reliably prevented from erroneously setting the infusion tube 200 in the reverse direction.

Subsequently, a structural example of the opening/closing cover 5 illustrated in FIG. 3 will be described.

As illustrated in FIG. 3, the opening/closing cover 5 is a plate-like member made with a thin molding resin member in order to achieve weight reduction of the infusion pump 1. In this manner, the weight of the opening/closing cover 5 can be reduced, and thus, the structure thereof can be simplified. The opening/closing cover 5 is supported by two hinge portions 2H and 2H with respect to the main body lower portion 2B of the main body cover 2 so as to be able to be in open and closed states and to cover the tube setting portion 50 along the CS-direction and the CR-direction having the rotary shaft 5A as the center. The two hinge portions 2H and 2H are arranged so as to respectively correspond to a first hook member 5D and a second hook member 5E.

As illustrated in FIGS. 2 and 3, an opening/closing operation lever 260 is provided on an upper right portion of the opening/closing cover 5 on an outer surface side. An infusion tube pressing member 500, the first hook member 5D, and the second hook member 5E are provided inside the opening/closing cover 5. The infusion tube pressing member 500 is arranged as a protruding portion having an elongated rectangular and planar shape along the X-direction. The infusion tube pressing member 500 is at a position facing the liquid delivering drive unit 60. The infusion tube pressing member 500 has a flat surface in the X-direction along the liquid delivering drive unit 60. A portion of the infusion tube 200 is pressedly interposed between the infusion tube pressing member 500 and the liquid delivering drive unit 60 when the opening/closing cover 5 is in the closed state in the CR-direction.

A health care worker can set the infusion tube 200 in the lower half portion of the main body of the infusion pump 1 along a horizontal direction while confirming display contents displayed on the display unit 3. After the infusion tube 200 is set in the tube setting portion 50, the opening/closing cover 5 can cover the infusion tube 200.

As illustrated in FIG. 3, the first hook member 5D and the second hook member 5E are respectively and mechanically interlocked with fixing portions 1D and 1E on the main body lower portion 1B side at the same time. Thus, as illustrated in FIG. 2, the opening/closing cover 5 maintains the tube setting portion 50 at the main body lower portion 1B in a shut-down state. The first hook member 5D and the second hook member 5E including the fixing portions 1D and 1E on the main body lower portion 1B side are configured to form a double-hook structure portion 300 of the opening/closing cover 5.

The tube clamp portion 270 illustrated in FIG. 3 clamps an intermediate portion of the infusion tube 200 so as to be occluded by causing the opening/closing cover 5 to be in the closed state. The tube clamp portion 270 is arranged in the vicinity of the fixing portion 1E on the left side, that is, at a position corresponding to the second hook member 5E on the left side. As a health care worker sets the infusion tube 200 horizontally in the X-direction and the health care worker causes the opening/closing cover 5 to be in the closed state in the CR-direction, the tube clamp portion 270 can cause an intermediate portion of the infusion tube 200 to be occluded.

As illustrated in FIG. 3, the first infusion tube guide portion 54 is provided at a portion on the right to the main body lower portion 1B, and the second infusion tube guide portion 55 is provided at a portion on the left to the main body lower portion 1B. An upstream side 200A of the infusion tube 200 fits the first infusion tube guide portion 54 so as to be able to be held, and a downstream side 200B of the infusion tube 200 fits the second infusion tube guide portion 55 so as to be able to be held. Thus, the infusion tube 200 is held in the horizontal direction along the X-direction. In this manner, the infusion tube 200 held in the horizontal direction is fixed by being fit along the air bubble sensor 51, the upstream occlusion sensor 52, the liquid delivering drive unit 60, the downstream occlusion sensor 53, and the tube clamp portion 270 in the T-direction.

As illustrated in FIG. 3, the second infusion tube guide portion 55 is a groove portion formed in a side surface portion 1S of the main body lower portion 1B, thereby holding a portion of the downstream side 200B of the infusion tube 200 in a detachably interposed manner. Accordingly, the first infusion tube guide portion 54 and the second infusion tube guide portion 55 can be reliably set in the tube setting portion 50 without nipping and squashing the infusion tube 200 between the opening/closing cover 5 and the tube setting portion 50.

The air bubble sensor 51 illustrated in FIG. 3 is a sensor which detects air bubbles (air) generated in the infusion tube 200. For example, the air bubble sensor 51 is an ultrasonic sensor which monitors air bubbles included in the drug flowing inside of the infusion tube 200 from outside the infusion tube 200 of soft vinyl chloride or the like formed of a thermoplastic resin such as polybutadiene and the like. Since transmittance of an ultrasonic wave of the drug and transmittance of an ultrasonic wave of air bubbles are different from each other, an ultrasonic wave receiving unit detects the difference therebetween to monitor whether or not air bubbles are present by irradiating the drug flowing inside of the infusion tube 200 with an ultrasonic wave generated from an ultrasonic wave oscillation unit of the ultrasonic sensor. The air bubble sensor 51 has a pressing member 320 and a receiving member 330. The ultrasonic wave oscillation unit is arranged in the pressing member 320. The ultrasonic wave receiving unit is arranged in the receiving member 330.

The upstream occlusion sensor 52 illustrated in FIG. 3 is a sensor which detects whether or not the inside of the infusion tube 200 is occluded on the upstream side 200A of the infusion tube 200. The downstream occlusion sensor 53 is a sensor which detects whether or not the inside of the infusion tube 200 is occluded on the downstream side 200B of the infusion tube 200. The upstream occlusion sensor 52 and the downstream occlusion sensor 53 have the same configuration. As a case of occlusion in the infusion tube 200, high viscosity of a drug to be delivered and a high concentration of the drug are exemplified.

As illustrated in FIG. 3, on an inner surface side of the opening/closing cover 5, pressing members 452 and 453 are provided respectively at positions corresponding to the upstream occlusion sensor 52 and the downstream occlusion sensor 53. As a health care worker covers the infusion tube 200 with the opening/closing cover 5 as illustrated in FIG. 2 after setting the infusion tube 200 in the tube setting portion 50 as illustrated in FIG. 3, the pressing member 452 and the pressing member 453 on the opening/closing cover 5 side can press portions of the infusion tube 200 respectively against the side of the upstream occlusion sensor 52 and the downstream occlusion sensor 53. Therefore, even though an infusion tube 200 of any size among multiple types of the infusion tubes 200 having diameters different from one another is set in the infusion pump 1, the upstream occlusion sensor 52 and the downstream occlusion sensor 53 can detect an occlusion state of the infusion tube 200 by causing the opening/closing cover 5 to be in the closed state.

Figure 4:
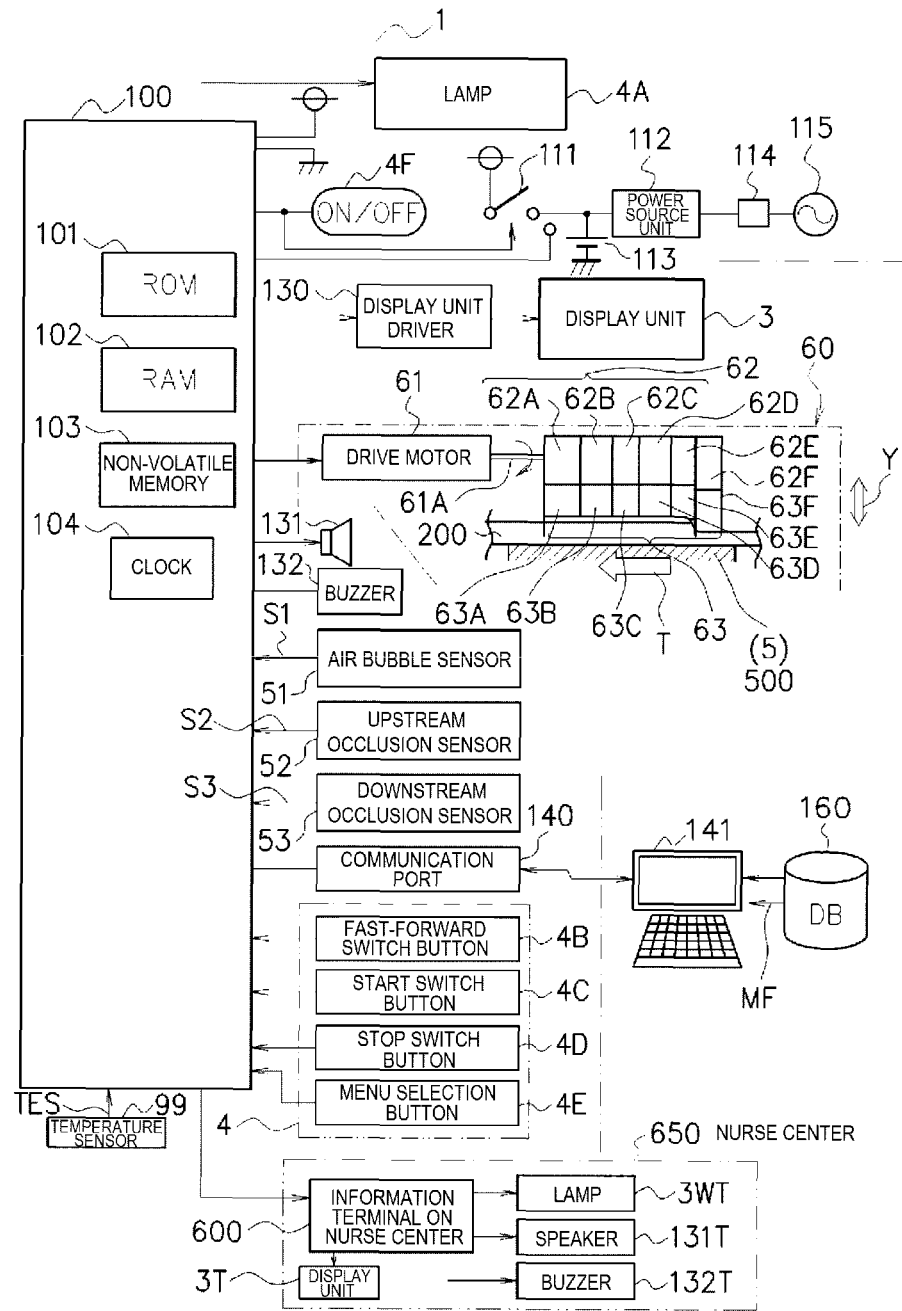
FIG. 4 is a diagram illustrating an example of an electrical configuration of the infusion pump.

FIG. 4 illustrates an example of an electrical configuration of the infusion pump 1.

As illustrated in FIG. 4, the infusion pump 1 has a control unit 100 which discriminates and controls overall operation of the infusion pump 1. The liquid delivering drive unit 60 includes a drive motor 61, a cam structure body 62 having a plurality number of cams which are rotationally driven by the drive motor 61, and a finger structure body 63 having a plurality of fingers which are respectively moved by the cams of the cam structure body 62.

The cam structure body 62 includes the plurality of cams, for example, a plurality of cams 62A to 62F. The finger structure body 63 has a plurality of fingers 63A to 63F respectively corresponding to the plurality of cams 62A to 62F. The plurality of cams 62A to 62F are arrayed so as to be respectively applied with phase differences. The cam structure body 62 is interlocked with an output shaft 61A of the drive motor 61.

As the drive motor 61 and the output shaft 61A of the drive motor 61 in the liquid delivering drive unit 60 rotate in response to a command from the control unit 100 illustrated in FIG. 4, the eccentric cams 62A to 62F provided in the cam structure body 62, which is pivotally supported by the output shaft 61A, rotate, thereby causing the plurality of fingers 63A to 63F to sequentially move back and forth in the Y-direction in one or more predetermined strokes (distance between the top dead center and the bottom dead center). A step motor is used as the drive motor 61.

As the plurality of fingers 63A to 63F sequentially move back and forth in the Y-direction on one or more predetermined strokes, the infusion tube 200 is pressed against the infusion tube pressing member 500 of the opening/closing cover 5 along the T-direction. Therefore, drug inside the infusion tube 200 can be delivered in the T-direction. In other words, the plurality of fingers 63A to 63F are individually driven, and the plurality of fingers 63A to 63F sequentially press an outer circumferential surface of the infusion tube 200 along the T-direction, thereby delivering drug inside the infusion tube 200. In this manner, in accordance with the control unit 100 controlling peristaltic movements of the plurality of fingers 63A to 63F, the fingers 63A to 63F sequentially move back and forth as if waves ripple so as to move an occluded point of the infusion tube 200 in the T-direction, and the infusion tube 200 is squeezed. Thus, drug is delivered to the inside of a blood vessel of the patient P through the indwelling needle 172.

The control unit 100 of the infusion pump 1 employs a central processing unit (CPU) chip. In order to determine and control the overall operation, the control unit 100 employs a one-chip microcomputer, for example, and includes a read-only memory (ROM) 101, a random access memory (RAM) 102, a non-volatile memory 103, and a clock 104. In the clock 104, the current time can be corrected through a predetermined operation. In addition, the current time can be acquired, an elapsed time of predetermined delivery can be measured, and a reference time for controlling a delivery rate can be measured, for example.

The control unit 100, illustrated in FIG. 4, is connected to a power switch button 4F, a switch 111 for switching power, a display unit driver 130, the display unit 3, the drive motor 61, a speaker 131, a buzzer 132, a lamp 3W, the air bubble sensor 51, the upstream occlusion sensor 52, the downstream occlusion sensor 53, a communication port 140, the operation panel (the operation buttons) 4, a temperature sensor 99, and an information terminal 600 on a nurse center side, thereby performing management and controlling of the peripheral components. At least any one or all of the display unit 3, the speaker 131, the buzzer 132, and the lamp 4A (formed with an LED, blinking or being lit in green during a normal operation, and blinking or being lit in red during an abnormal operation) which functions as an operation indicator, are warning means for issuing a warning to a health care worker in response to a command from the control unit 100, as the control unit 100 recognizes an occurrence of an occlusion in the infusion tube 200. Accordingly, the health care worker can promptly recognizes an occlusion in the infusion tube 200, and thus, it is possible to stop the drive motor 61 of the infusion pump 1 and to stop the operation for delivering the drug.

The temperature sensor 99 detects a temperature of an environment where the infusion pump 1 is placed, and transmits a temperature signal (TES) to the control unit 100.

The switch 111 performs switching between a power converter unit 112 and a battery 113 so as to supply power to the control unit 100 from any one of the power converter unit 112 and the battery 113. The power converter unit 112 is connected to a commercial AC power source 115 through a power plug 114. The battery 113 is a secondary battery, such as a rechargeable/dischargeable lithium-ion battery and the like, for example.

The control unit 100 is also connected to the upstream occlusion sensor 52 and the downstream occlusion sensor 53. Accordingly, the control unit 100 can monitor an occlusion state inside the infusion tube 200 as well.

Figure 5:
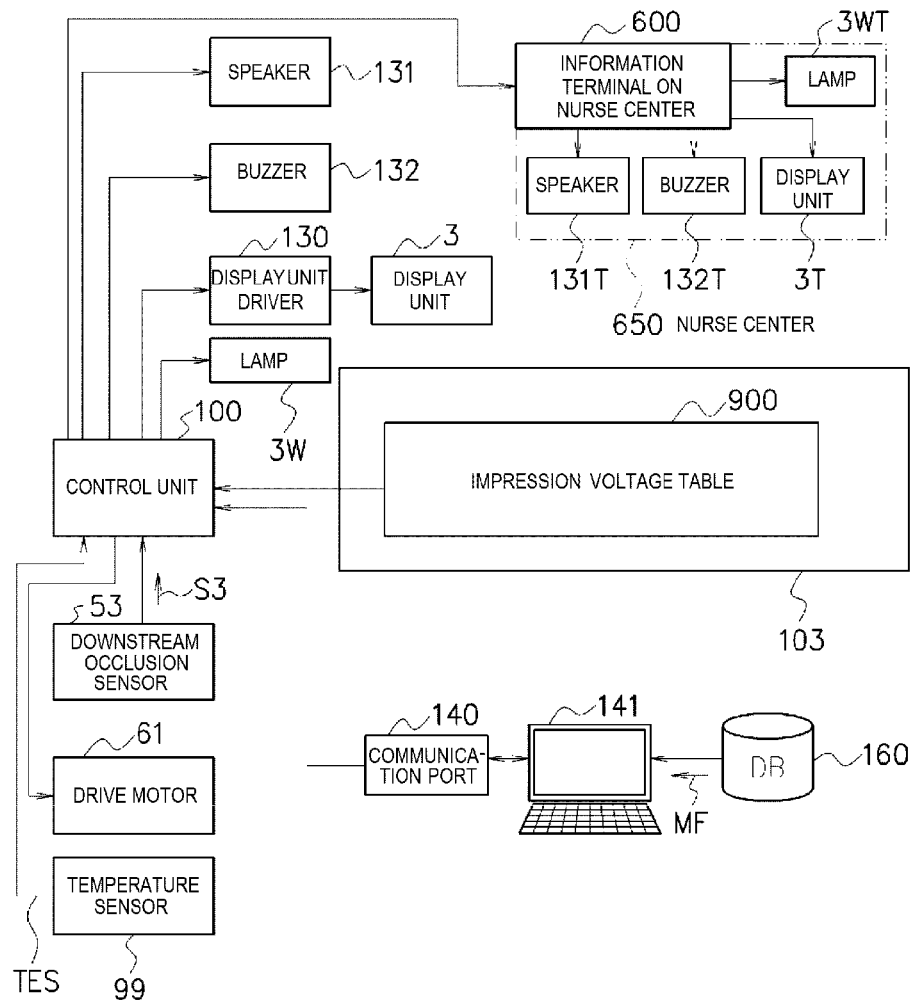
FIG. 5 is a block diagram illustrating a portion in the example of the electrical configuration of the infusion pump illustrated in FIG. 4, in more detail.

As illustrated in FIGS. 4 and 5, when the infusion pump 1 is located in a hospital ward, for example, the information terminal 600 on the nurse center side is located at a nurse center 650 away from the infusion pump 1. The information terminal 600 includes a display unit 3T, a lamp 3WT, a speaker 131T, and a buzzer 132T similar to the display unit 3, the lamp 4A, the speaker 131, and the buzzer 132, which are mentioned above. At least any one or all of the display unit 3T, the speaker 131T, the buzzer 132T, and the lamp 3WT are the warning means for issuing a warning to a health care worker in response to a command from the control unit 100 as the control unit 100 recognizes an occurrence of an occlusion in the infusion tube 200. Accordingly, the health care worker at the nurse center 650 can promptly recognize an occlusion in the infusion tube 200, and thus, it is possible to stop the drive motor 61 of the infusion pump 1 and to stop the operation for delivering the drug.

The display unit driver 130, in FIG. 4, drives the display unit 3 in response to a command from the control unit 100 and displays contents of information exemplified in FIG. 2 or a warning message. For example, by lighting the backlight of the light emitting diode (LED), the display can change from "a yellow display screen" to "a white display screen" which is a warning screen issued to a health care worker. Accordingly, a possibility of being visually recognized by a health care worker is enhanced. The lamp 4A for displaying errors is lit in response to a command from the control unit 100. The speaker 131 can notify a health care worker of various contents of warnings through audio in response to a command of the control unit 100. The buzzer 132 can notify a health care worker of various warnings through a sound in response to a command of the control unit 100.

Similarly, the display unit 3T is driven in response to a command from the control unit 100, and contents of information exemplified in FIG. 2 or a warning message is displayed. For example, by lighting the backlight of the light emitting diode (LED), the display can change from "a yellow display screen" to "a white display screen" which is a warning screen issued to a health care worker. Accordingly, the possibility of being visually recognized by a health care worker is enhanced. The lamp 4A for displaying errors blinks or is lit in red in response to a command from the control unit 100. The speaker 131T can notify a health care worker of various contents of warnings through audio in response to a command of the control unit 100. The buzzer 132T can notify a health care worker of various warnings through a sound in response to a command of the control unit 100.

In FIG. 4, the control unit 100 is supplied with an air bubble detection signal S1 from the air bubble sensor 51, an upstream occlusion signal S2 from the upstream occlusion sensor 52 indicating that the infusion tube 200 is occluded on the upstream side, and a downstream occlusion signal S3 from the downstream occlusion sensor 53 indicating that the infusion tube 200 is occluded on the downstream side.

The upstream occlusion sensor 52 and the downstream occlusion sensor 53 can detect a state where an internal pressure of an infusion circuit exceeds a set pressure inside the infusion pump 1 so that drug cannot be delivered. The state where an internal pressure of the infusion circuit exceeds the set pressure inside the infusion pump 1 is caused when so-called "slippage of a needle" occurs, that is, a distal end of the indwelling needle 172 for infusion illustrated in FIG. 2 slips out from the inside of a blood vessel of the patient P, when the inside of the infusion tube 200 is occluded due to blockage, when a portion of the infusion tube 200 is squashed and bent, when a drug having high viscosity is used, and the like.

In FIG. 4, the control unit 100 can communicate bi-directionally with a computer 141, such as a desktop computer, through the communication port 140 via RS-232C (RS: Recommended Standard; a serial input/output interface of a communication method standardized by EIA (Electronic Industries Association)), a cable communication method, wireless LAN, infrared communication, and the like. The computer 141 is connected to drug database (DB) 160. A drug library MF stored in the drug database 160 can be acquired by the control unit 100 through the computer 141 as necessary, and can be stored in the non-volatile memory 103 of the control unit 100. The control unit 100 can display the drug library MF and the like on the display unit 3 illustrated in FIG. 2, for example, based on the stored drug library MF.

As the drug information MF, the name of a manufacturer of the drug, the name of the drug, the upper and lower limits for a planned dosage quantity (mL) of the drug, the upper and lower limits for a flow rate (mL/h), contraindicated information and the like are exemplified.

In reference to FIG. 4, the upstream occlusion sensor 52 illustrated in FIG. 4 is a sensor for detecting whether or not the inside of the infusion tube 200 is occluded on the upstream side 200A of the infusion tube 200 and for transmitting the upstream occlusion signal S2 to the control unit 100 indicating that the upstream side of the infusion tube 200 is occluded. When the upstream side 200A of the infusion tube 200 in FIG. 2 is occluded, even though the drug 171 tends to flow from the drug bag 170 filled with the drug 171 illustrated in FIG. 2 to the upstream side 200A of the infusion tube 200 through the Klemme 179, since the infusion tube 200 is occluded due to the occlusion on the upstream side 200A and the liquid delivering drive unit 60 is driven, a portion on the immediately downstream side of the upstream side 200A is under a negative pressure. In contrast, the downstream occlusion sensor 53 is a sensor for detecting whether or not the inside of the infusion tube 200 is occluded on the downstream side 200B of the infusion tube 200 and for transmitting the downstream occlusion signal S3 indicating that the downstream side of the infusion tube 200 is occluded. When the downstream side 200B of the infusion tube 200 in FIG. 2 is occluded, since the drug 171 delivered from the upstream side by the driven liquid delivering drive unit 60 cannot be delivered due to occlusion of the downstream side 200B, the inside of the downstream side 200B is under a positive pressure.

Figure 6:
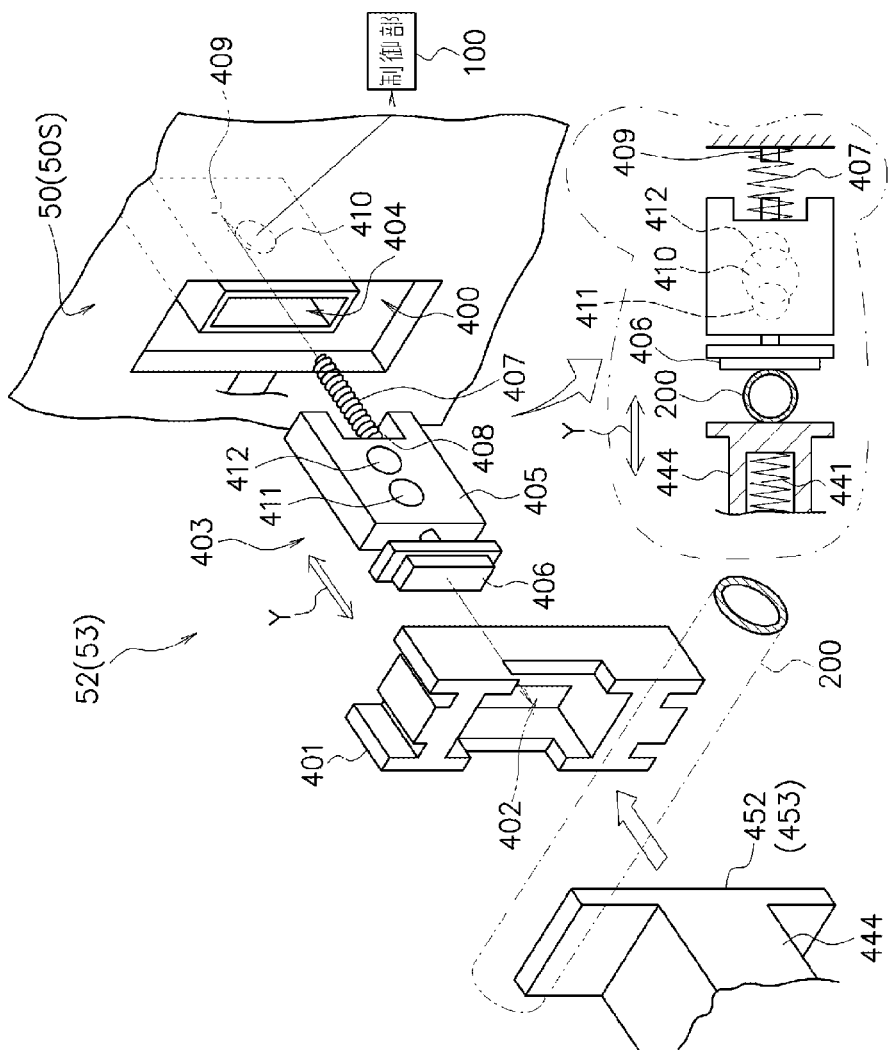
FIG. 6 is an exploded perspective view illustrating a structural example of an upstream occlusion sensor and a downstream occlusion sensor.

FIG. 5 is a block diagram illustrating a portion in the example of the electrical configuration of the infusion pump 1 illustrated in FIG. 4, in more detail. FIG. 6 is an exploded perspective view illustrating a structural example of the upstream occlusion sensor 52 and the downstream occlusion sensor 53.

As illustrated in FIG. 5, an impression voltage table 900 is previously stored in the non-volatile memory 103 of the control unit 100, for example. The temperature sensor 99 is connected to the control unit 100.

As exemplified in FIG. 6, the upstream occlusion sensor 52 and the downstream occlusion sensor 53 have the same structure. A hole portion 400 is provided on a surface 50S of the tube setting portion 50. A plastic frame member 401 fits the hole portion 400, and a frame member 401 has a rectangular opening portion 402. A plastic plunger 403 is inserted into an accommodation hole portion 404 inside the hole portion 400. The plunger 403 has a base portion 405, a distal end portion 406, and a spring 407.

The distal end portion 406 of the plunger 403 fits the opening portion 402. One end portion of the spring 407 is attached to the base portion 405, and the other end portion of the spring 407 is attached to a protrusion 409 inside the accommodation hole portion 404. A Hall element 410 is arranged on an inner surface of the accommodation hole portion 404. Two magnets 411 and 412 are arranged in the base portion 405.

With such a structure, the upstream occlusion sensor 52 and the downstream occlusion sensor 53 can be simply set onto the surface 50S of the tube setting portion 50 by only setting the frame member 401 in the hole portion 400 and causing the base portion 405 to be inserted into the opening portion 402 and the accommodation hole portion 404 while holding the spring 407. Thus, workability of assembling the upstream occlusion sensor 52 and the downstream occlusion sensor 53 is improved.

Meanwhile, as illustrated in FIG. 4, the pressing members 452 and 453 are respectively provided at positions corresponding to the upstream occlusion sensor 52 and the downstream occlusion sensor 53 on an inner surface side of the opening/closing cover 5. Each of the pressing members 452 and 453 is structured to be pressed to the facing frame member 401 side through a spring 441. The pressing member 452 is a first pressing member, and the pressing member 453 is a second pressing member.

As a health care worker covers the infusion tube 200 with the opening/closing cover 5, as illustrated in FIG. 2, after setting the infusion tube 200 in the tube setting portion 50, as illustrated in FIG. 3, the first pressing member 452 and the second pressing member 453 on the opening/closing cover 5 side can press portions of the infusion tube 200 respectively against the side of the upstream occlusion sensor 52 and the downstream occlusion sensor 53. Therefore, even though the outer diameter of the infusion tube 200 is slightly uneven due to manufacturing tolerance or the infusion tube 200 is a product of a different manufacturer, as the infusion tube 200 is closed by the opening/closing cover 5, the upstream occlusion sensor 52 and the downstream occlusion sensor 53 are surely pressed against the infusion tube 200. Thus, it is possible to accurately detect an occlusion state of the infusion tube 200.

Structures of the upstream occlusion sensor 52 and the downstream occlusion sensor 53 will be described in more detail. When the opening/closing cover 5 is in the closed state as illustrated in FIG. 2, the infusion tube 200 is interposed and held between the pressing member 452 (453) and the distal end portion 406 of the plunger 403 by each biasing force of the springs 407 and 441 as the biasing members, as illustrated in FIG. 6. The plunger 403 is an example of a movement member which is linearly movable with respect to the Hall element 410. If the diameter of the infusion tube 200 varies due to an occlusion of the infusion tube 200, the distal end portion 406 moves in the Y-direction following after the varied diameter of the infusion tube 200. Therefore, since the magnets 411 and 412 move with respect to the Hall element 410, the Hall element 410 can detect a variation in a magnetic flux, thereby transmitting a movement distance of the plunger 403 to the control unit 100 as a signal of a variation in a magnetic flux.

As illustrated in FIG. 6, a central axis direction of the spring 441 and a central axis direction of the spring 407 coincide with each other. Therefore, the springs 441 and 407 can apply a pressurizing force to the infusion tube 200 along the infusion tube 200 in a radial direction by interposing the infusion tube 200 between the pressing member 452 (453) and the distal end portion 406. Therefore, it is possible to accurately detect an occlusion state of the infusion tube 200 by detecting the movement distance of the plungers 403 forming the occlusion sensors 52 and 53.

Figure 7A:
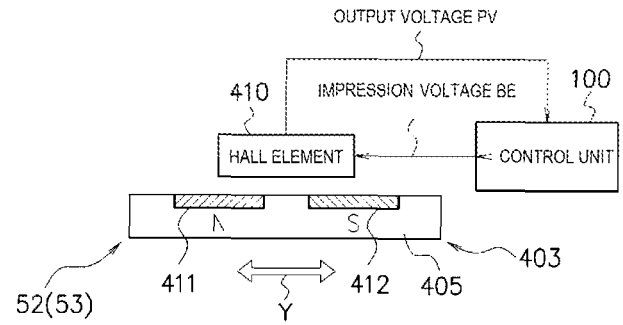
FIG. 7A is a diagram illustrating magnets arranged in a base portion of a plunger, and a Hall element. The diagram illustrates an example of an increase of an output voltage value of the Hall element with respect to an increase of a movement distance of the plunger.

FIG. 7(A) illustrates the magnets 411 and 412 arranged in the base portion 405 of the plunger 403 illustrated in FIG. 6 and the Hall element 410. The magnets 411 and 412 arranged in the base portion 405 are moving bodies which are movable in the Y-direction, and the Hall element 410 is a fixed body. Therefore, when diametral dimensions of the infusion tube 200 varies due to an occlusion of the infusion tube 200, the distal end portion 406, in FIG. 6, moves in the Y-direction following after the diametral variation of the infusion tube 200 so that the magnets 411 and 412 move in the Y-direction with respect to the Hall element 410. The Hall element 410 detects a variation in the magnetic flux in response to linear movements of the magnets 411 and 412 in the Y-direction. The Hall element 410 is supplied with an impression voltage BE from the control unit 100. As the Hall element 410 detects a variation in the magnetic flux from the magnets 411 and 412, an output voltage PV of the Hall element 410 is transmitted to the control unit 100. The output voltage PV of the Hall element 410 is proportional to the movement distance of the plunger 403 in the Y-direction. Gradients formed by the output voltages PV in FIGS. 7(B) and 7(C) may be reversed (gradient downward to the right).

Figure 7B:
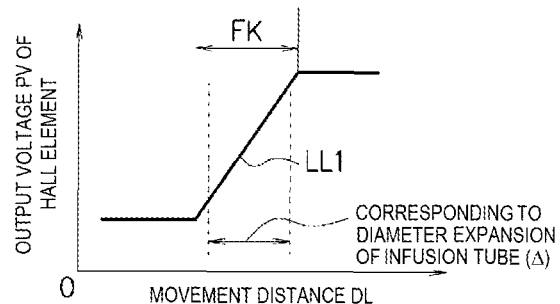
FIG. 7B is a diagram that illustrates an example of an increase of an output voltage value of the Hall element with respect to an increase of a movement distance of the plunger.
Figure 7C:
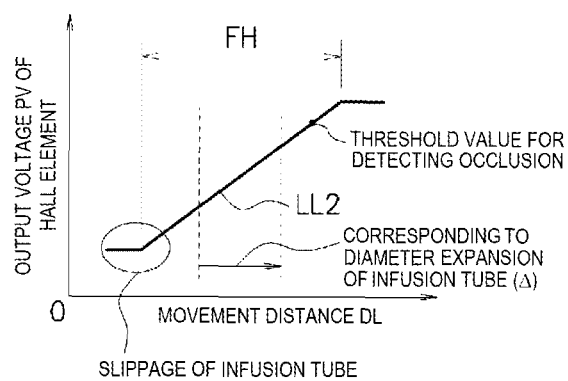
FIG. 7C is another diagram that illustrates an example of an increase of an output voltage value of the Hall element with respect to an increase of a movement distance of the plunger.

FIGS. 7(B) and 7(C) illustrate examples of relationship between the output voltage PV of the Hall element 410 of the upstream occlusion sensor 52 and the downstream occlusion sensor 53, and a movement distance DL of the plunger 403 corresponding to swelling (diameter expansion Δ=an increase of the outer diameter of approximately 0.2 mm) of the outer diameter (approximately 3.3 mm) of the infusion tube 200 caused by an occlusion.

In each example illustrated in FIGS. 7(B) and 7(C), in the relationship between the output voltage PV of the Hall element 410 and the movement distance DL of the plunger 403, the output voltages PV are substantially the same in a straight line (linear). However, when a straight line section FK in the case of FIG. 7(B) and a straight line section FH in the case of FIG. 7(C) are compared, a relationship of the straight line section FK<(is less than) the straight line section FH is established. In other words, the gradient of a linear portion LL1 in the case of FIG. 7(B) is greater than the gradient of a linear portion LL2 in the case of FIG. 7(B).

When setting the upstream occlusion sensor 52 and the downstream occlusion sensor 53 illustrated in FIG. 6 in the infusion pump 1, to set the relationship between the output voltage PV of the Hall elements 410 in the upstream occlusion sensor 52 and the downstream occlusion sensor 53, and the movement distance DL of the plunger 403 to a linear relationship having appropriate sensitivity which is not too high or not too low, setting processing is performed as follows.

Figure 8:
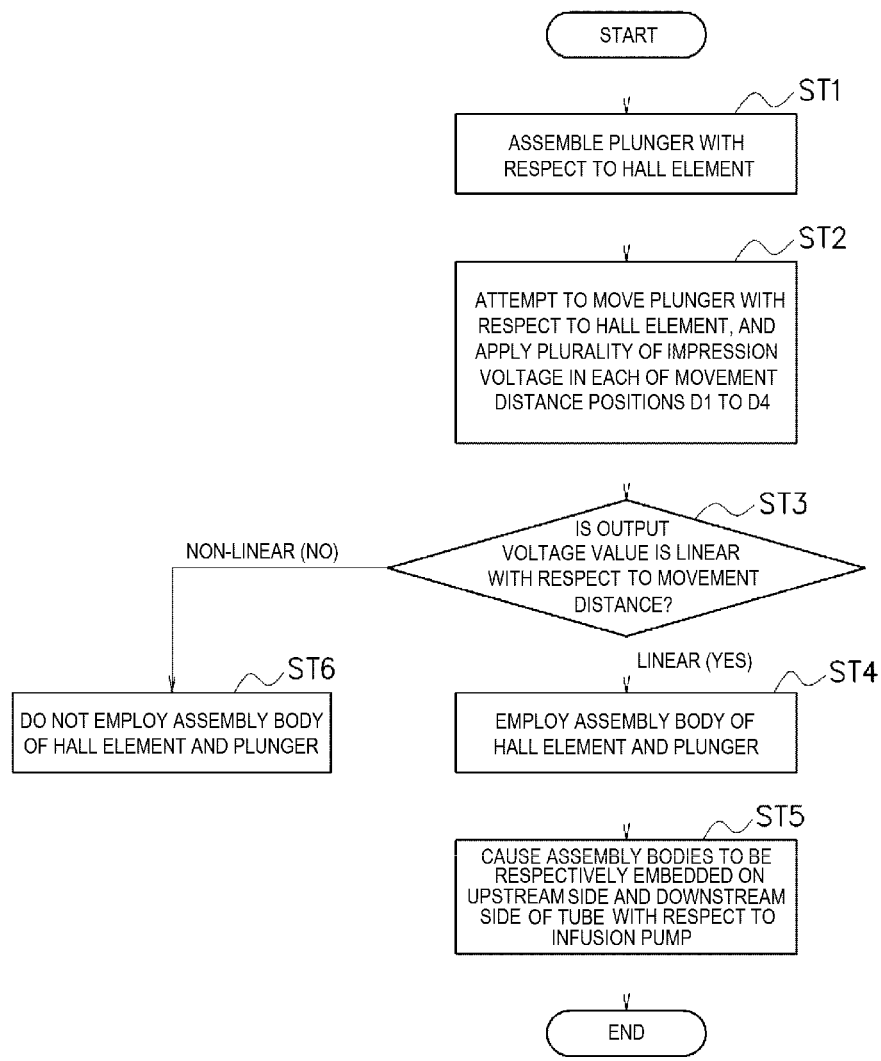
FIG. 8 is a flowchart illustrating a procedure for setting a relationship between an output voltage PV of the Hall element and a movement distance DL of the plunger to an appropriate linear relationship when assembling and setting the upstream occlusion sensor and the downstream occlusion sensor in the infusion pump.
Figure 9:
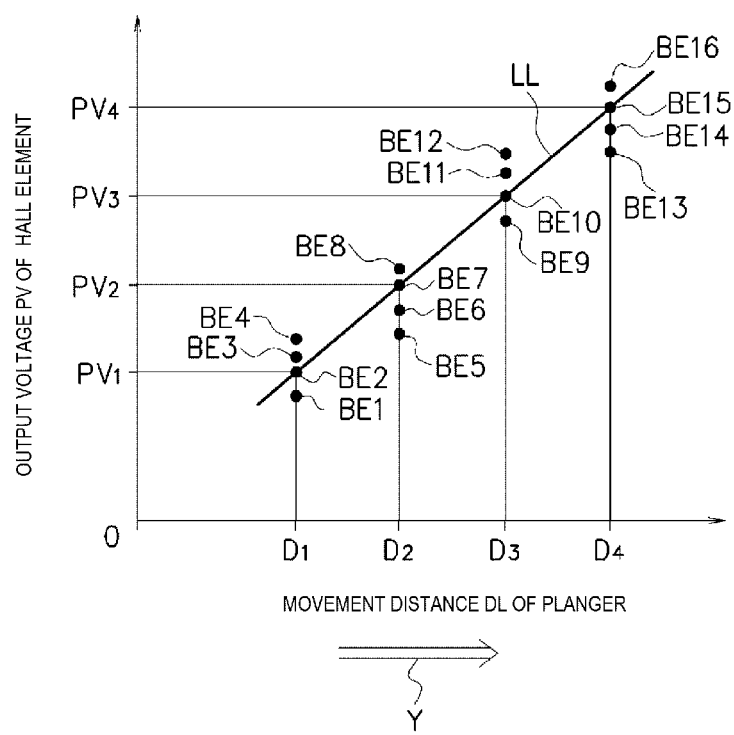
FIG. 9 is a diagram illustrating a state where the relationship between the output voltage PV of the Hall element and the movement distance DL of the plunger is set to an appropriate linear relationship in each of the upstream occlusion sensor and the downstream occlusion sensor.

FIG. 8 illustrates a procedure for setting the relationship between the output voltage PV of the Hall element 410 and the movement distance DL of the plunger 403 to the linear relationship having appropriate sensitivity when assembling the upstream occlusion sensor 52 and the downstream occlusion sensor 53 and setting the sensors in the infusion pump 1. FIG. 9 illustrates a state where the relationship between the output voltage PV of the Hall elements 410 in the upstream occlusion sensor 52 and the downstream occlusion sensor 53, and the movement distance DL of the plunger 403 is set to the linear relationship having appropriate sensitivity (appropriate gradient of the straight line portion).

In Step ST1 illustrated in FIG. 8, when an assembler assembles the upstream occlusion sensor 52 and the downstream occlusion sensor 53 as illustrated in FIG. 6, the Hall element 410 is fixed to a predetermined position in the accommodation hole portion 404 of the hole portion 400. The Hall element 410 is electrically connected to the control unit 100. Therefore, as illustrated in FIG. 7(A), the control unit 100 is in a state capable of supplying the impression voltage BE to the Hall element 410.

As illustrated in FIG. 6, the assembler inserts the plunger 403 into the accommodation hole portion 404 inside the hole portion 400 and causes the distal end portion 406 of the plunger 403 to fit the opening portion 402 of the frame member 401. One end portion of the spring 407 is attached to the base portion 405, and the other end portion of the spring 407 is attached to the protrusion 409 in the accommodation hole portion 404.

In Step ST2 of FIG. 8, when the assembler manually moves the plunger 403 illustrated in FIG. 6 in the Y-direction against a force of the spring 407, the movement distance DL of the plunger 403 is positioned by sequentially moving to four preset movement distance positions D1, D2, D3, and D4, for example, along the Y-direction, as exemplified in FIG. 9.

With reference to the impression voltage table 900, the control unit 100 in FIG. 5 supplies impression voltages BE1 to BE16 stored in the impression voltage table 900 to the Hall element 410. In other words, the control unit 100 supplies the impression voltages BE1 to BE4 to the Hall element 410 at the time when the movement distance DL of the plunger 403 is positioned at the movement distance position D1. The control unit 100 supplies the impression voltages BE5 to BE8 to the Hall element 410 at the time when the movement distance DL of the plunger 403 is positioned at the movement distance position D2. The control unit 100 supplies the impression voltages BE9 to BE12 to the Hall element 410 at the time when the movement distance DL of the plunger 403 is positioned at the movement distance position D3. Then, the control unit 100 supplies the impression voltages BE13 to BE16 to the Hall element 410 at the time when the movement distance DL of the plunger 403 is positioned at the movement distance position D4.

Then, in Step ST3 of FIG. 8, the control unit 100 acquires an output voltage PV1 of the Hall element by selecting an impression voltage BE2 at the time when the movement distance DL of the plunger 403 is positioned at the movement distance position D1 in FIG. 9. An output voltage PV2 of the Hall element is acquired by selecting an impression voltage BE7 at the time when the movement distance DL of the plunger 403 is positioned at the movement distance position D2. An output voltage PV3 of the Hall element is acquired by selecting an impression voltage BE10 at the time when the movement distance DL of the plunger 403 is positioned at the movement distance position D3. Then, an output voltage PV4 of the Hall element is acquired by selecting an impression voltage BE15 at the time when the movement distance DL of the plunger 403 is positioned at the movement distance position D4. Accordingly, it is possible to obtain accurate linearity of the movement distance DL of the plunger 403 as indicated by a straight line LL, based on the relationship of the movement distance positions D1, D2, D3, and D4 corresponding to the output voltages PV1, PV2, PV3, and PV4 of the Hall element. The control unit 100 can obtain the output voltage PV of the Hall element corresponding to the position at any position of the movement distance DL of the plunger 403, from the straight line LL obtained as described above.

In this case, as the case in FIG. 7(B), if the movement distance DL is small with respect to the output voltage PV in which an output of linearity can be obtained by the upstream occlusion sensor 52 and the downstream occlusion sensor 53, the movement distance DL which can be used for detection by the plunger 403 becomes short. Therefore, unless the length of the plunger 403 in the Y-direction can be sufficiently utilized, an occlusion state in a swelling rate (diameter expansion 4) of the infusion tube 200 is less likely to be detected. In other words, there is a little margin for accurately detecting an occlusion. Therefore, to make the plunger 403 able to accurately detect an occlusion as much as possible, as illustrated in FIG. 7(C), the movement distance DL is caused to be approximately twice the output voltage PV in which an output of linearity can be obtained by the upstream occlusion sensor 52 and the downstream occlusion sensor 53 similarly to that in FIG. 7(B). A distance of the straight line section FH which can be used for detection by the plunger 403 is caused to be 2 to 3 times a swelling rate (diameter expansion $\Delta$) of the infusion tube 200.

The distance smaller than twice thereof results in the case of FIG. 7(B), and thus an occlusion state is less likely to be detected. The distance greater than three times thereof results in an increase of dimensions of the plunger 403 in the Y-direction, which is not preferable.

In this manner, that is, it is possible not only to increase a margin with respect to a threshold value in detection of occlusion and to achieve appropriate sensitivity so as to allow detection of occlusion to be accurate but also to provide a plurality of the threshold values in detection of occlusion as necessary. The four predetermined movement distance positions D1, D2, D3, and D4 are set as the movement distance DL of the plunger 403. However, five or more movement distance positions may be set in advance so as to acquire five or more output voltages PV of the Hall element 410 corresponding to the five or more movement distance positions.

In a case of being smaller than the movement distance position D1 and/or in a case where the output voltage PV deviates from a linear region, it is detected to be in a state where the infusion tube 200 is not reliably set in the tube setting portion 50 of the liquid delivering drive unit 60, or a state where the infusion tube 200 deviates from the tube setting portion 50 of the liquid delivering drive unit 60, which is the predetermined position to be set, during a delivering operation. Therefore, it is possible to generate an alarm and stop the drive motor.

In Step ST3, as a result of discrimination by the control unit 100, if the relationship between an increase of the movement distance DL of the plunger 403 and an increase of the output voltage PV of the Hall element 410 is the linear relationship, and the relationship between the output voltage PV of the Hall elements 410 in the upstream occlusion sensor 52 and the downstream occlusion sensor 53 and the movement distance DL of the plunger 403 can be set to the linear relationship having appropriate sensitivity which is not too high or not too low, the procedure proceeds to Step ST4.

In Step ST4, an assembler can employ an assembly body of the plunger 403 and the Hall element 410. In Step ST5, the upstream occlusion sensor 52 and the downstream occlusion sensor 53 illustrated in FIG. 6 can be installed. In this manner, setting of the plunger 403 can be reliably performed. Thus, it is possible to shorten a time for embedding and setting the upstream occlusion sensor 52 and the downstream occlusion sensor 53.

In Step ST3 as a result of discrimination by the control unit 100, if the relationship between an increase of the movement distance DL of the plunger 403 and an increase of the output voltage PV of the Hall element 410 is not the linear relationship, the assembly body of the plunger 403 and the Hall element 410 is considered to be a defective product, thereby not being employed, in step ST6. For example, another plunger 403 is prepared to execute the procedure from Step ST1 to Step ST3 in FIG. 8 by using the assembly body of the plunger 403 which is newly prepared, and the Hall element 410.

Incidentally, even though an internal pressure generated by action of drug delivered in the infusion tube 200 is constant, a swelling rate (shrunk on the upstream occlusion sensor 52 side, and swollen (expands in diameter) on the downstream occlusion sensor 53 side) of the infusion tube 200 varies in accordance with a variation of the peripheral temperature of the infusion tube 200. The infusion tube 200 is formed of a thermoplastic resin such as polybutadiene and the like. The infusion tube 200 tends to be softened under a high temperature, whereas the infusion tube 200 tends to be hardened under a low temperature. Therefore, even though a constant internal pressure is acting in the tube, if the environmental temperature where the infusion pump 1 is located rises, the infusion tube 200 is likely to swell, whereas if the environmental temperature where the infusion pump 1 is located falls, the infusion tube 200 is less likely to swell.

Therefore, preferably, there is provided the temperature sensor 99, such as, a thermistor or the like exemplified in FIG. 5 to detect the environmental temperature where the infusion pump 1 is used. Then, a factor, associated with the temperature (detected by the temperature sensor), is changed for every 5° C. between 0° C. to 40° C., for example, for a threshold value (a threshold value of the movement distance of the plunger 403 forming the occlusion sensors 52 and 53) for occlusion pressure detection. Thus, an occlusion state of the infusion tube 200 can be accurately detected. For example, the movement distances are stored in the read-only memory (ROM) 101 causing the movement distance of the plunger 403 at the time of a constant pressure and a temperature range of 20° C. to 25° C. to be 1, the movement distance of the plunger 403 at the time of a temperature range of 15° C. to 20° C. to be 0.99, the movement distance of the plunger 403 at the time of a temperature range of 10° C. to 15° C. to be 0.98, the movement distance of the plunger 403 at the time of a temperature range of 0° C. to 15° C. to be 0.97, the movement distance of the plunger 403 at the time of a temperature range of 25° C. to 30° C. to be 1.01, and the movement distance of the plunger 403 at the time of a temperature range of 30° C. to 35° C. to be 1.02, thereby changing the threshold value.

Accordingly, even though the infusion tube 200 is likely to swell or less likely to swell, an occlusion pressure inside the infusion tube 200 can be detected at a substantially constant level in response to the swelling or contracting of the infusion tube 200. A correction may be performed by increasing the levels at which the factor is changed by more than 5° C. However, in this case, sensitivity of occlusion detection is slightly degraded. A correction may be performed by decreasing the levels at which the factor is changed by more than 5° C. However, in this case, a storage volume of the ROM (the read-only memory) 101 increases.

Subsequently, a usage example of the above-described infusion pump 1 will be briefly described.

As illustrated in FIG. 3, when causing the opening/closing cover 5 to be in an open state and setting the infusion tube 200 in the tube setting portion 50, a health care worker visually confirms a setting direction of the infusion tube 200 while watching the infusion tube setting direction display portion 150. Then, a health care worker arranges the upstream side 200A of the infusion tube 200 at a portion to the right in the main body portion 1B on the first infusion tube guide portion 54 side, and arranges the downstream side 200B of the infusion tube 200 at a portion to the left in the main body portion 1B on the second infusion tube guide portion 55 side.

In this manner, a health care worker can set the infusion tube 200 in the T-direction along the first infusion tube guide portion 54, the air bubble sensor 51, the upstream occlusion sensor 52, the liquid delivering drive unit 60, the downstream occlusion sensor 53, the tube clamp portion 270, and the second infusion tube guide portion 55. Thereafter, as illustrated in FIGS. 1 and 2, the opening/closing cover 5 is caused to be in a closed state, thereby covering the air bubble sensor 51, the upstream occlusion sensor 52, the downstream occlusion sensor 53, the liquid delivering drive unit 60, and the tube clamp portion 270. Accordingly, the infusion tube 200 can be set along the T-direction, which is the proper direction, and thus, the drug can be delivered along the T-direction through the infusion tube 200 by driving the liquid delivering drive unit 60.

The infusion pump 1 can be an infusion pump for delivering a drug to the inside of a blood vessel of a patient by using the infusion tube. The infusion pump 1 includes the occlusion sensor that detects an occlusion of the infusion tube when delivering the drug and the control unit that is supplied with an output voltage of the occlusion sensor. The occlusion sensor includes the movement member which has the plurality of magnets and is arranged in a linearly movable manner. The occlusion sensor also includes the Hall element, which is fixed to the infusion pump on the main body side, detects a variation in magnetic fluxes of the plurality of magnets generated in accordance with a linear movement of the movement member following a variation of the infusion tube in the radial direction that results from the occlusion of the infusion tube, and changes the variation of the infusion tube in the radial direction into the output voltage. When increasing a movement distance of the movement member to the plurality of predetermined positions, the control unit obtains linearity of the output voltage of the Hall element with respect to the movement distances to the plurality of positions by applying the plurality of predetermined impression voltages to the Hall element for each of the movement distances to the plurality of positions so as to select from the plurality of impression voltages applied for each of the movement distances to the plurality of positions.

Accordingly, when increasing the movement distance of the movement member to the plurality of predetermined positions, the control unit is configured to obtain linearity of the output voltage of the Hall element with respect to the movement distances to the plurality of positions by applying the plurality of predetermined impression voltages to the Hall element for each of the movement distances to the plurality of positions so as to select from the plurality of impression voltages applied for each of the movement distances to the plurality of positions. Accordingly, linearity of the output voltage of the Hall element in the occlusion sensor with respect to a variation of the movement distance of the movement member, that is, a variation of the infusion tube in diametral dimensions can be accurately obtained, and an occlusion state of the infusion tube can be accurately detected.

The control unit has the impression voltage table storing the plurality of predetermined impression voltages which are preset for each of the movement distances to the plurality of positions. Accordingly, with reference to the impression voltage table, the control unit can apply the plurality of predetermined impression voltages which are preset to the Hall element for each of the movement distances to the plurality of positions, and thus, linearity of the output voltage of the Hall element in the occlusion sensor with respect to a variation of the infusion tube in diametral dimensions can be simply obtained.

Since the warning means which issues a warning in response to a command of the control unit when the occlusion sensor detects an occlusion of the infusion tube, a health care worker can be informed of the occlusion state of the infusion tube through the warning. Thus, in a case of occlusion, the delivering operation can be immediately stopped.

Since the temperature sensor which detects an environmental temperature of the infusion tube is included, and control unit changes a threshold value of the movement distance of the movement member in response to a signal from the temperature sensor in accordance with a value of the environmental temperature, an occlusion of the infusion tube can be detected in accordance with a swelling state of the infusion tube in the radial direction depending on the environmental temperature.

The display unit displaying information and the operation panel portion having the operation buttons are arranged in the upper portion of the main body of the infusion pump, and the infusion tube for delivering the drug is arranged in a region of the lower portion of the main body of the infusion pump. Accordingly, a health care worker can perform delivering of drug by using the infusion pump while confirming the information on the display unit in the upper portion of the main body. Then, the health care worker can operate the operation button of the operation panel portion while confirming the information on the display unit in the upper portion of the main body.

The infusion pump can be also applied for delivering blood (a blood transfusion) and delivering a nutrient from the intestinal tract in addition to delivering a drug.

The embodiments are is not limited to those described above, and thus, various changes and modifications can be made without departing from the scope of the Claims.

Each configuration in the above-described embodiments can be partially omitted and can be arbitrarily combined so as to be different from above.

REFERENCE SIGNS LIST

1 . . . infusion pump,
3 . . . display unit,
50 . . . tube setting portion,
52 . . . upstream occlusion sensor,
53 . . . downstream occlusion sensor,
60 . . . liquid delivering drive unit,
100 . . . control unit,
200 . . . infusion tube,
403 . . . plunger (example of movement member),
410 . . . Hall element, and
411, 412 . . . magnets.

The invention claimed is:

1. An infusion pump for delivering one of a drug, blood, and a nutrient to a patient through an infusion tube, the infusion pump comprising:
an occlusion sensor that detects an occlusion of the infusion tube when delivering the one of the drug, blood, and the nutrient, wherein the occlusion sensor includes a movement member which has a plurality of magnets and is arranged in a linearly movable manner, wherein the occlusion sensor includes a Hall element, fixed to a tube setting portion of the infusion pump on a side of a main body, wherein the Hall element detects a variation in magnetic fluxes of the plurality of magnets, wherein the magnetic fluxes vary in accordance with a linear movement of the movement member, wherein the linear movement is caused by a variation of the infusion tube in a radial direction that results from the occlusion of the infusion tube, and wherein the occlusion sensor changes the variation of the infusion tube in the radial direction into an output voltage of the Hall element;
a control unit that is supplied with the output voltage of the Hall element of the occlusion sensor, wherein, when increasing a movement distance of the movement member to a plurality of predetermined positions, the control unit is configured to obtain linearity of the output voltage of the Hall element with respect to the movement distances to the plurality of predetermined positions by applying a plurality of predetermined impression voltages to the Hall element for each of the movement distances to the plurality of positions so as to select from the plurality of predetermined impression voltages applied for each of the movement distances to the plurality of predetermined positions.

2. The infusion pump according to claim 1, wherein the movement distance corresponding to the output voltage having linearity is 2 to 3 times a swelling rate of the infusion tube.

3. The infusion pump according to claim 1, wherein the control unit determines that the infusion tube deviates from a tube setting portion if the output voltage is not in a region of linearity.

4. The infusion pump according to claim 1, wherein the control unit has an impression voltage table storing the plurality of predetermined impression voltages which are respectively predetermined for each of the movement distances to the plurality of predetermined positions.

5. The infusion pump according to claim 1, further comprising: a warning means that issues a warning in response to a command of the control unit if the occlusion sensor detects an occlusion of the infusion tube.

6. The infusion pump according to claim 1, further comprising: a temperature sensor that detects a peripheral temperature where the infusion tube is located, wherein the control unit changes a threshold value of the movement distance of the movement member in response to a signal from the temperature sensor in accordance with a value of the peripheral temperature.

7. The infusion pump according to claim 1, further comprising:
a display unit configured to display information; and
an operation panel portion having an operation button arranged in an upper portion of the main body of the infusion pump.

8. The infusion pump according to any one of claim 1, wherein the infusion tube for delivering the drug, blood, or the nutrient is arranged in a region of a lower portion of the main body of the infusion pump.

* * * * *